Figure 1:
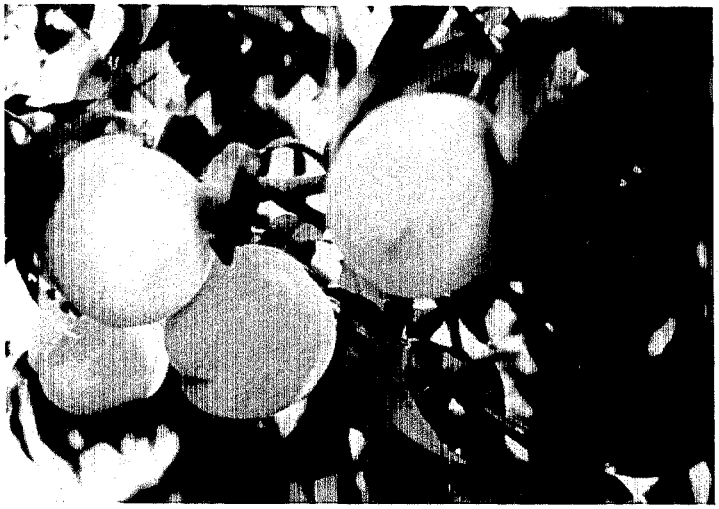

US00PP09895P

United States Patent [19]

Friday

[11] Patent Number: Plant 9,895

[45] Date of Patent: May 20, 1997

[54] PEACH TREE 'P.F. 24-007'

[75] Inventor: Paul J. Friday, P.O. Box 850, Coloma, Mich. 49038

[73] Assignee: Paul J. Friday, Coloma, Mich.

[21] Appl. No.: 585,913

[22] Filed: Jan. 16, 1996

[51] Int. Cl.[6] ..... A01H 5/00

[52] U.S. Cl. ..... Plt./43.2

[58] Field of Search ..... Plt./43.2

*Primary Examiner*—James R. Feyrer
*Attorney, Agent, or Firm*—Fred P. Kostka

[57] ABSTRACT

A new and distinct variety of peach *Prunus pessica,* tree having the following unique combination of desirable features:

1. The new and distinct variety of peach tree is of moderate upright growth and a regular and productive bearer of large peaches having a diameter of between about 2½" and 3".
2. Producing a very firm fruit having a resilient flesh texture.
3. Blossoms are partially showy when in full bloom.
4. A substantially spherical fruit with skin of lavender-red color overlying a light to whitish yellow at maturity.
5. Mid-season maturing fruit of good taste.
6. A mid-season maturing fruit of good storage and shelf life.

1 Drawing Sheet

ORIGIN OF VARIETY

The new peach tree (herreinafter referred to as the P.F. 24-007 peach tree) was originated by Paul Friday in the experimental orchard, which is maintained for the purpose of breeding peach trees, at Paul Friday Farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this applications, P.F. 24-007, was a selection from one such a seedling population, and was based on the numerous superior genetic attributes of this tree which are described in the botanical descriptions to follow. While not exhaustive, the botanical descriptions to follow are believed to represent a reasonably complete botanical description of the new peach tree which is sufficiently detailed to distinguish the tree from the most closely related trees within the same market class.

ASEXUAL REPRODUCTION OF THE VARIETY

The new and distinct variety of peach tree was asexually propagated by budding as performed in the experimental orchard of Paul Friday Farms Inc., located in Coloma, Mich. The asexual propagation demonstrates that such reproduction of the characteristics of the tree are consistent and are established and transmitted through succeeding propagation.

SUMMARY OF THE VARIETY

The new and distinct variety of peach tree is of large upright growth and a regular and productive bearer of peaches. A distinct characteristic of the P.F. 24-007 peach tree is its vigorous growth. The blossoms are characterized by being contracted or partially spread when in full bloom. At the same time the petals of the blossoms are of lesser length than the length of petals of the normal showy blossom as exemplified by the Loring peach blossom.

The blossoms of the present peach tree at full bloom may be characterized as being partially non-showy.

The fruit at maturity is large, having flesh of very clear yellow with red around the pit and slight red color into the flesh.

The skin is smooth having moderate down and is of slightly lavender to purple-red color overlying light or whitish yellow. At maturity the peach is spherical having an average diameter ranging between about 2½" to 3".

The fruit has a firm flesh and may be described as resilient to the extent that the flesh is yieldable and restorable to its original state when subjected to impact forces which may cause permanent deformities in peaches of the commercial varieties. The firmness of the fruit facilitates handling and packaging of the peaches without damaging the same for shipment. This results in less spoilage and also increases the shelf life.

The fruit matures in the mid-part of the peach growing season of southwestern Michigan. The fruit as mentioned heretofore is of slightly lavender to purple-red color overlying light or whitish yellow and has a very attractive appearance.

BRIEF DESCRIPTION OF THE PHOTOGRAPHS

In the drawing, in FIG. 1, taken at a maturity stage of firm ripe for harvest on Aug. 25, 1995, shows typical wood of fruiting age, with four whole specimens of fruit attached to stems at different angles. The rounded fruit shape, the depth and variable character of sutures, the exceptional symmetry of the fruit; and, the color of the extensive solid blush and slightly mottled over-color patterns are depicted over the ground color of the fruit skin. Stem color, the foliage are also shown.

Figure 2:
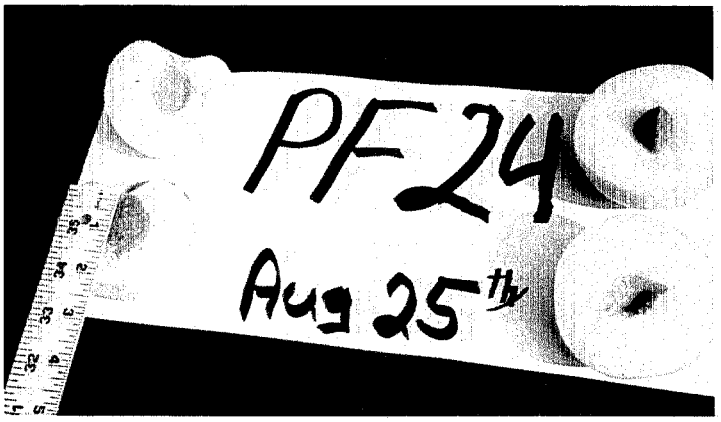

In FIG. 2, on the left, a specimen of fruit is depicted which has been split along the suture plane, with the stone remaining in the half at the bottom left. A ruler has been placed over the half of the fruit shown at the bottom to depict the size of the fruit and the stone. A second specimen on the right has been split on a plane ninety degrees to the suture plane to depict the fruit flesh in cross section. The conformance of the pit cavity is illustrated as is the desirable ratio of the size of the stone to the fruit size of this tree.

Figure 3:
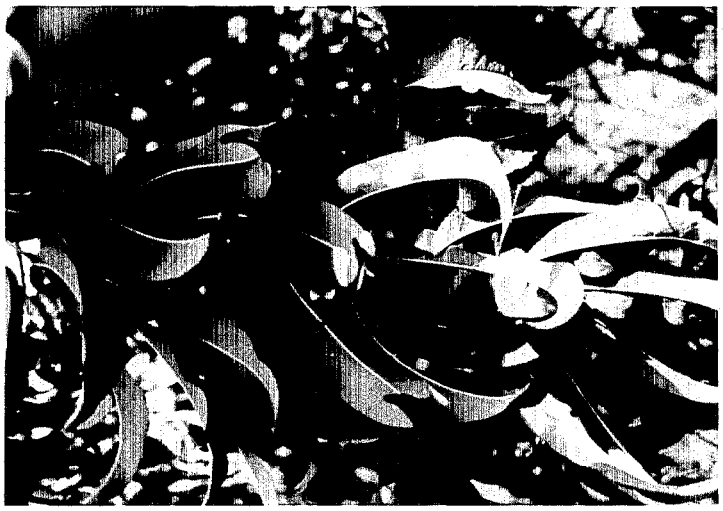

In FIG. 3 of the drawing, stems of current season's growth are depicted at a stage of about harvest season; and shows bark coloration, the under sides of leaves; the shape, color and character of the leaves; and, internode length.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Panatone Matching System (PMS) as used internationally to identify printed colors.

Tree:
- *Height.*—Unpruned 20'.
- *Width.*—Unpruned 16'.
- *Size.*—Large.
- *Vigor.*—Medium to very vigorous.
- *Density.*—Heavy, requires substantial pruning.
- *Form.*—Upright.
- *Production.*—Productive, requires some thinning to obtain size described.
- *Bearer.*—Consistent.
- *Disease resistance to bacterial leaf and fruit spot.*—Very good.

Trunk:
- *Size.*—Medium to stocky.
- *Surface.*—Smooth to medium shaggy.

Branches:
- *Size.*—Medium.
- *Surface.*—Smooth to medium.
- *Lenticels.*—Substantial number of medium size.
- *Color.*—Gray.

Leaves:
- *Size.*—Medium. Average length — 6½". Average width — 1½".
- *Form.*—Lanceolate — pointed.
- *Thickness.*—Medium.
- *Texture.*—Medium.
- *Margin.*—Serrate.
- *Petiole.*—Medium length — medium thickness.
- *Gland.*—0 to 1 on each side of the leaf base or upper portion of petiole, very small or partial when present.
- *Color.*—Upper surface: green (350c). Bottom: dull green (349c).

Flower buds:
- *Size.*—Medium.
- *Length.*—Medium.

Flowers:
- *Blooming period.*—May 1, 1995 to May 6, 1995.
- *Size.*—Medium to large, 1¼" diameter.
- *Pollen.*—Present, self-fertilizing.
- *Color.*—Pink.

Fruit:
- *Maturity when described.*—Firm ripe.
- *Date of first picking.*—Aug. 20. 1995. Fruit matures very evenly and can be harvested in two to three pickings.
- *Date of last picking.*—Aug. 27, 1995.
- *Size.*—Large sphere, notably large — 95% of the fruit is 2½" or larger in diameter and over half is 2¾" or larger, and a substantial amount of fruit is 3" in diamter or larger.
- *Form.*—Spherical.
- *Suture.*—Medium.

Skin:
- *Thickness.*—Medium.
- *Texture.*—Medium.
- *Tendency to crack.*—None.
- *Down.*—Moderate.
- *Color.*—Slightly lavender to purple-red (207u), background color light or whitish yellow (600u).

Flesh:
- *Texture.*—Firm — non-melting.
- *Ripens.*—Relatively even.
- *Flavor.*—Excellent.
- *Aroma.*—Pleasant.
- *Eating quality.*—Excellent.
- *Color.*—Very clear yellow (107u), red around pit and slight red color into flesh (179u).

Stone:
- *Type.*—Freestone.
- *Size.*—Average length — 1½". Average width — 1". Average thickness — ¾".
- *Form.*—Ovid.
- *Base.*—Straight.
- *Apex.*—Pointed.
- *Sides.*—Nearly equal.
- *Surface.*—Furrowed.
- *Color.*—Reddish brown (492c).
- *Tendency to crack.*—Slight, about 3%.

Use: Desert.
Shipping quality: Excellent.
Keeping quality: Excellent.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as illustrated and described as a large size tree, a consistent bearer of lavender-red colored, large fruit for the mid-season peach growing season, said fruit at maturity being of spherical shape with firm flesh.

* * * * *